United States Patent [19]

Reijonen

[11] 4,187,148
[45] Feb. 5, 1980

[54] PROCEDURE FOR SEPARATING AND RECOVERING MARSH GAS

[75] Inventor: Veli E. Reijonen, Helsinki, Finland

[73] Assignee: VYR-Metoder AB, Taby, Sweden

[21] Appl. No.: 845,623

[22] Filed: Oct. 26, 1977

Related U.S. Application Data

[63] Continuation of Ser. No. 590,702, Jun. 26, 1975, abandoned.

[51] Int. Cl.$^2$ .............................................. C12D 3/10
[52] U.S. Cl. ................................... 48/197 R; 55/58; 435/167
[58] Field of Search ..................... 195/27, 33, 103.5 P; 48/196 R, 197, 197 A; 55/58

[56] References Cited

U.S. PATENT DOCUMENTS

| | | | |
|---|---|---|---|
| 1,990,523 | 2/1935 | Buswell et al. | 195/27 |
| 4,022,665 | 5/1977 | Ghosh et al. | 195/27 |

OTHER PUBLICATIONS

Beerstecher, Petroleum Microbiology p. 5, Elsevier Press Inc., New York 1954.
Underkofler et al., Industrial Fermentations, vol. II, pp. 518–539, Chemical Pub. Co., Inc., N.Y. 1954.
Hobson et al., Critical Reviews In Environmental Control 4:1, pp. 156, 157, 186–188 (1974).

*Primary Examiner*—Alvin E. Tanenholtz
*Attorney, Agent, or Firm*—Haseltine, Lake & Waters

[57] ABSTRACT

A procedure for separating and recovering marsh gas from bog mud. The marsh gas is separated from the mud by conducting the mud into a separating space carrying a pressure lower than the pressure prevailing in the bog, and from which space the gas separating from the mud is conducted to a place of storage or of use.

2 Claims, No Drawings

PROCEDURE FOR SEPARATING AND RECOVERING MARSH GAS

This is a continuation of application Ser. No. 590,702, filed June 26, 1975, now abandoned.

March gas, which consists of methane (usually more than 90%), hydrogen sulfide, nitrogen, ammonia etc., is a source of energy having a high calorific value. At present, separation and recovery of marsh gas from bog mud is practiced by allowing the marsh gas of itself to bubble up to the bog surface, whence it is gathered by means of a bell-like collecting apparatus for use as household gas. It follows that such gathering is exceedingly slow and cumbersome and only small gas quantities are gained. As a consequence the present significance of march gas as an enrgy source is altogether minor and nearly nil.

It has now been found in studies that have been made, that in spite of the small amount of gas separating from a bog the bog mud may contain marsh gas, that is methane in the first place, in solution even up to 1 g per liter of bog mud. The high quantity of methane present dissolved in the bog mud is due to the capacity of water to solve large amounts of methane and to the high hydrostatic pressure, up to several atmospheres, prevailing at greater depth in the bog, which increases the partial pressure of methane dissolved in the mud. One may then observe that bogs contain abundant, unutilized methane stores. Only the part exceeding the methane saturation limit of the bog mud is separable and recoverable by the methods of the prior art.

The methane in the marsh gas emerges as a result of organic activity of the so-called methane bacteria. These bacteria include *Sarcina methanica*, Pseudosarcina, *Methanobacterium formicium, M. omelianskii, M. propionicum, M. sönngenii, M. suboxydans, Methanococcus mazei, M. vannelii, Methanosarcina methanica* and *M. barkerii*.

It has been found in studies which have been made, that the pH value in bogs is usually about 4, while methane bacteria thrive best at somewhat higher pH values. It has further been found that bogs lack trace elements, and nutrients required in the vital processes of methane bacteria. It follows that the formation of methane in bog areas is rather slow and therefore economically insignificant.

The aim of the present invention is to eliminate the drawbacks mentioned. The procedure of the invention is characterized in that the marsh gas is separated from the mud by conducting the mud into a separation space carrying a pressure lower than the pressure prevailing in the bog, and conducting the gas separating from the mud in said space to the place of storage or use.

When this is done, the partial pressure of the marsh gas in the bog mud decreases, owing to the pressure lower than that in the bog which prevails in the separating space, and the quantity of gas in excess of the gas saturation limit under the conditions in the separating space separates in gaseous form from the mud. Obviously the proportion of marsh gas that can be separated from the mud is greater the lower the pressure in the separating space. It is then most appropriate to carry in the separating space a subatmospheric pressure.

The mud may advantageously be conducted from the separating space back to the bog after the marsh gas has been separated from it. The mud will then once more be subjected to the effect of methane bacteria in the anaerobic conditions prevailing under the bog.

In an advantageous embodiment of the invention, nutrient and trace element substances required by the methane bacteria are added to the bog. The activity of methane bacteria may further be promoted by adding to the bog phosphorus, potassium and/or nitrogen fertilizer. It is likewise possible to add to the bog one or several of the following trace elements: iron, manganese, magnesium, calcium, nickel, cobalt, copper, zinc, and/or molybdenum.

The conditions of life of methane bacteria may further be improved by adjusting the pH value of the bog mud to be within pH 5 to 8. This is because methane bacteria have been found to be active within this range, appropriately when pH is 5 to 8, and most appropriately in the range from pH 7.2 to 8.0. Adjustment of the pH value to desired value is practicable by adding to the bog slaked or unslaked lime.

The substances meant to added to the bog may appropriately be added to the mud that is being conducted from the separating space back to the bog. When this is done, the separation of marsh gas from bog mud and the addition of nutrient and trace element substances as well as buffering agents to the mud takes place in a continuous cyclic process, which yields marsh gas with a high methane content as long as there are stores of the organogenic substances needed by the methane bacteria.

In studies that have been carried out, the procedure of the invention for separation and recovery of marsh gas from bog mud has been found to operate eminently well, and the formation of methane has then been observed to take place without interruptions and even with explosive force.

The invention shall be illustrated in the following with the aid of examples, though without confining it in any way.

EXAMPLE 1

In an experiment, in a two-liter glass bottle there was placed 1 l of water, in which 0.5 kg of bog peat was suspended. The temperature of the suspension was 30° C., and its pH was found to be 4.6. Addition of calcium acetate and calcium carbonate was then made to the suspension, 5 mg of both. The consequence of the calcium salt addition was an increase of pH to 5.5 and formation of gas, which was found to contain 91% methane. The generation of gas continued throughout the test period at a rate of 35 to 50 ml per day. At the same time the pH of the suspension increased to 6.8. The experiment was kept running for two weeks.

EXAMPLE 2

In another experiment, mud was conducted from 5 m depth in a bog into a space carrying subatmospheric pressure and the marsh gas was separated in said space. The mud was pumped back into the bog down to 5 m depth, 4 m removed from the point where it had been drawn, and at the same time a nutrient substance was added to it. The mud quantity drawn from the bog to the separating space equalled that pumped from the separating space back to the bog, and it was 0.2 $m^3$ per min. (=288 $m^3$ per day). In the separating space the mud drawn from the bog was atomized, and the gas was separated from the liquid under 0.2 at. subatmospheric pressure. To the mud pumped back to the bog calcium salts were added at 1 gram equivalent per $m^3$ mud. In the separating space marsh gas separated from the mud at 60 kg per day, and it contained about 92% methane.

I claim:

1. A process for producing and recovering marsh gas generated from mud in a bog through bacterial activity comprising the steps of adding to the bog an adjusting chemical to adjust the pH value of the bog mud to be in the range from 5 to 8; adding to the bog a nutrient substance needed by methane bacteria, said substance being selected from the group consisting of phosphorus, potassium and nitrogen fertilizers; adding to the bog a trace element substance needed by methane bacteria, said substance being selected from the group consisting of iron, manganese, magnesium, calcium, nickel, cobalt, copper, zinc and molybdenum; conducting the mud from a depth having a hydrostatic pressure of several atmospheres into a separating space having subatmospheric pressure to separate the gas from the mud; conducting the gas to a place of storage or of use; and conducting the mud from the separating space back to the bog thus accomplishing a cyclic process where said adjusting chemical and said nutrient and trace element substances are added to the bog by means of adding them to the mud that is conducted back into the bog.

2. The process of claim 1 wherein $Ca(OH)_2$ or $CaO$ is added to the bog to adjust the pH value.

* * * * *